(12) United States Patent
Lee et al.

(10) Patent No.: US 10,058,261 B2
(45) Date of Patent: Aug. 28, 2018

(54) NONINVASIVE ATRIAL ACTIVITY ESTIMATION SYSTEM AND METHOD

(71) Applicants: KOREA INSTITUTE OF SCIENCE AND TECHNOLOGY, Seoul (KR); THE ASAN FOUNDATION, Seoul (KR)

(72) Inventors: Jong Min Lee, Gunpo-si (KR); Yoha Hwang, Seoul (KR); Seung-Jong Kim, Seoul (KR); Kyoung Jae Kim, Seoul (KR); Hyeong-jin Jeon, Seoul (KR); Gi-Byoung Nam, Seoul (KR); Yong-Giun Kim, Seoul (KR)

(73) Assignees: Korea Institute of Science and Technology, Seoul (KR); The Asan Foundation, Seoul (KR)

(*) Notice: Subject to any disclaimer, the term of this patent is extended or adjusted under 35 U.S.C. 154(b) by 0 days.

(21) Appl. No.: 14/471,762

(22) Filed: Aug. 28, 2014

(65) Prior Publication Data
US 2015/0133808 A1 May 14, 2015

(30) Foreign Application Priority Data
Nov. 13, 2013 (KR) .................. 10-2013-0137560

(51) Int. Cl.
*A61B 5/0456* (2006.01)
*A61B 5/0402* (2006.01)
*A61B 5/0452* (2006.01)

(52) U.S. Cl.
CPC .......... *A61B 5/0456* (2013.01); *A61B 5/0402* (2013.01); *A61B 5/0452* (2013.01)

(58) Field of Classification Search
CPC ..... A61B 5/04; A61B 5/04012; A61B 5/0402; A61B 5/0452
(Continued)

(56) References Cited

U.S. PATENT DOCUMENTS 6,615,075 B2 9/2003 Mlynash et al.
8,543,195 B1* 9/2013 Brockway ............ A61B 5/0402
600/300
(Continued)

FOREIGN PATENT DOCUMENTS

KR 10-2012-0133793 A 12/2012

OTHER PUBLICATIONS

Pan J, Tompkins WJ (1985) "A Real-Time QRS Detection Algorithm". IEEE Trans Biomed Eng 32: 230-236.*
(Continued)

*Primary Examiner* — Allen Porter, Jr.
(74) *Attorney, Agent, or Firm* — NSIP Law

(57) ABSTRACT

Provided is a non-invasive system for estimating an atrial signal, including a plurality of sensors to sense a surface electrocardiogram signal, a reference atrial signal generation unit to generate an estimated ventricular signal with respect to a R wave in an electrocardiogram signal from one sensor among the plurality of sensors, and to generate a reference atrial signal by subtracting the estimated ventricular signal from the electrocardiogram signal from the one sensor, and an atrial signal estimation unit to generate an estimated atrial signal by applying a constrained independent component analysis algorithm based on the reference atrial signal to the received surface electrocardiogram signal, and to estimate one of the estimated atrial signals as an actual atrial signal, and a method using the same.

18 Claims, 14 Drawing Sheets

(58) Field of Classification Search
USPC .......................................... 600/509, 519, 521
See application file for complete search history.

(56) References Cited

U.S. PATENT DOCUMENTS

| | | | |
|---|---|---|---|
| 2011/0137190 A1* | 6/2011 | Katz | A61B 5/0452 600/509 |
| 2011/0144705 A1 | 6/2011 | Milpied et al. | |
| 2014/0235996 A1* | 8/2014 | Kim | A61B 6/03 600/411 |

OTHER PUBLICATIONS

Lee, Jeon, et al. "Event synchronous adaptive filter based atrial activity estimation in single-lead atrial fibrillation electrocardiograms." Medical & Biological Engineering & Computing vol. 50 (2012): 801-811.

* cited by examiner

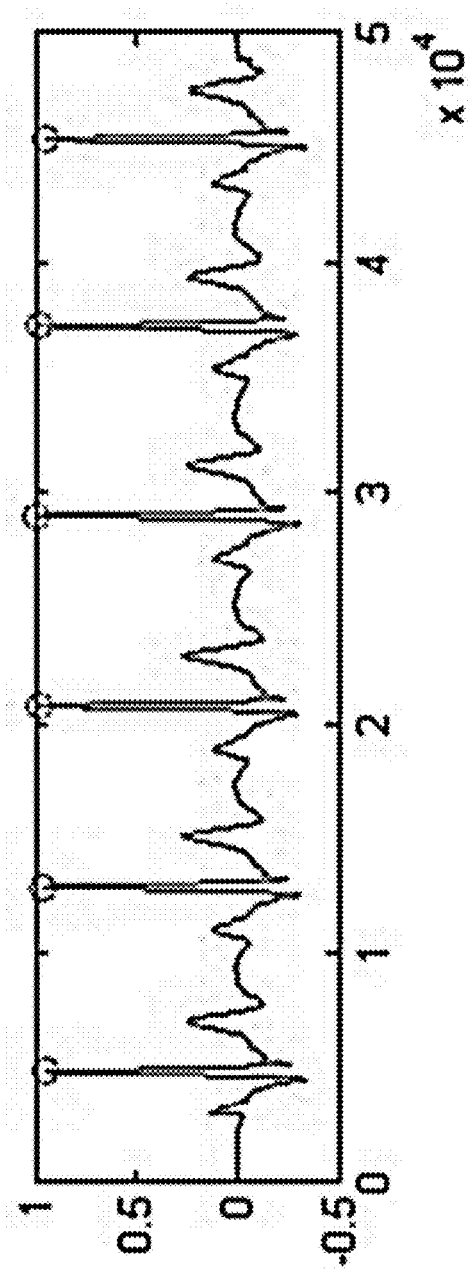

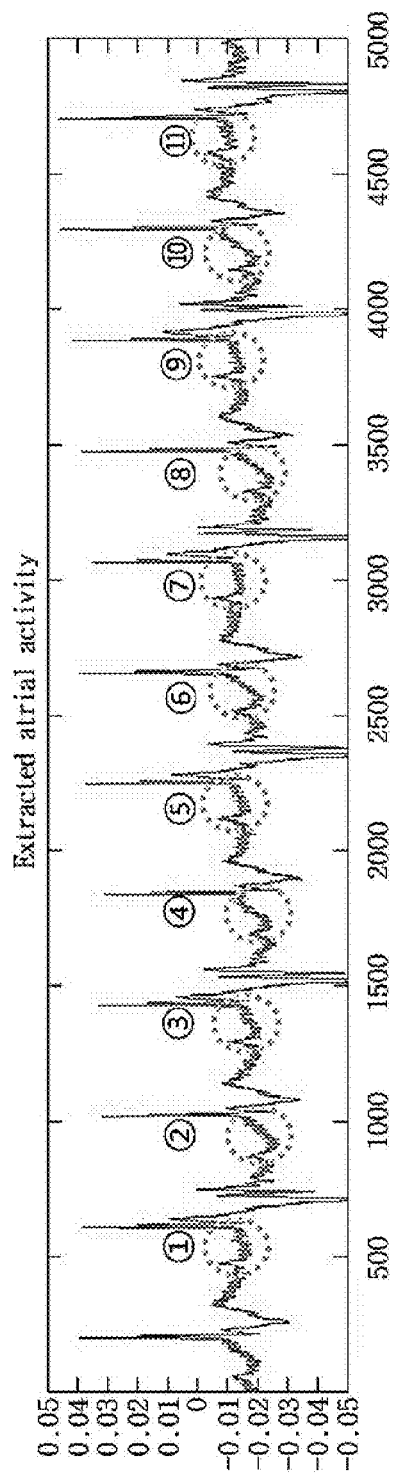

NONINVASIVE ATRIAL ACTIVITY ESTIMATION SYSTEM AND METHOD

CROSS-REFERENCE TO RELATED APPLICATION

This application claims priority to Korean Patent Application No. 10-2013-0137560, filed on Nov. 13, 2013, and all the benefits accruing therefrom under 35 U.S.C. § 119, the contents of which in its entirety are herein incorporated by reference.

BACKGROUND

1. Field

The present disclosure relates to a system and method that extracts an atrial signal from a surface electrocardiogram, and more particularly, to a system and method that extracts only a signal close to an atrial signal from a multi-lead surface electrocardiogram in which a ventricular signal and an atrial signal measured by a non-invasive method are mixed.

2. Description of the Related Art

FIG. 1 illustrates a typical electrocardiogram waveform. Here, a T wave represents a ventricular repolarization signal occurring after ventricular depolarization (QRS complex), and is used to predict a disease such as myocardinal ischemia, acute myocardinal infarction, myocarditis, pericarditis, ventricular hypertrophy, ventricular arrhythmia, and the like, by observing repetitive changes (alternation phenomenon) in width or height of the T wave every alternate cycle. This ventricular repolarization signal is being widely used because of having a large waveform and being visually distinguishable.

Similar to ventricular repolarization, atrial repolarization occurs after atrial depolarization (P wave). This atrial repolarization signal ($T_a$) is indicated by a dotted line in FIG. 1. However, as shown in FIG. 1, a $T_a$ wave is difficult to distinguish by eye due to having a small waveform and being hidden by a ventricular depolarization signal.

However, changes in width or height of a $T_a$ wave (alternation phenomenon) may be used as a predictive factor for a stroke, atrial fibrillation, atrial arrhythmia, a heart failure, an ischemic heart disease, and the like, and thus, a method of identifying a $T_a$ wave is required. Generally, to identify a $T_a$ wave, an invasive method is used, but an invasive method has a drawback of a burden for a patient or a complex procedure.

To overcome this drawback, an independent component analysis method generally used for signal separation may be used to measure a surface electrocardiogram signal and extract an atrial signal in a non-invasive manner. The independent component analysis method is a method which estimates signals closest to source signals to find an unmixing matrix able to separate the source signals from observed mixed signals, based on the assumption of mutual independence between the source signals in a state that prior knowledge of the source signals is unknown.

However, in case in which a conventional independent component analysis technique is used, the shortcoming is that it is impossible to understand what each separated signal represents and comparison of each signal is not easy due to different scales for each separated signal. That is, according to a general independent component analysis algorithm, there are problems that identifying an atrial signal among each output signal must rely on an intuitive decision by a physician and very different sizes of each output signal hamper a physician's making an intuitive decision. Also, to obtain only a particular signal, all signals need to be separated according to characteristics of an algorithm, requiring a large amount of computation. For these all reasons, a general independent component analysis algorithm is not suitable for an application field of the present disclosure.

Conventionally, to extract only an atrial signal from a surface electrocardiogram, an average beat subtraction method which estimates an atrial signal by removing a ventricular signal, that is, an ensemble average of a QRST waveform (FIG. 1) from a surface electrocardiogram has been widely used. However, because an average beat subtraction method estimates an atrial signal by subtracting a fixed QRST waveform in each electrocardiogram cycle, there is a limitation of a large residual error occurring when a QRST waveform changes over time.

Recently, to resolve this issue, attempts have been made to estimate an atrial signal by applying a principal component analysis or singular value decomposition technique. Both the two methods may estimate an atrial signal with a smaller residual error than a conventional average beat subtraction method. However, to resolve a signal discontinuity issue raised when finding elements corresponding to an atrial signal from a separated result or reconstructing an atrial signal by mapping these elements, a post-processing process is needed, taking statistical characteristics of a signal into account, and even though post-processing is performed, an error occurring when compensating for discontinuity may distort a P-$T_a$ waveform of a very small size.

More recently, a method of extracting an atrial signal from Holter electrocardiogram recording in a simple manner using an adaptive filter is proposed. Atrial fibrillation may be effectively diagnosed by calculating a delay time of a P wave in an atrial signal extracted through the proposed method and counting the number of occurrences. However, the extracted atrial signal is a signal for atrial fibrillation diagnosis, and is difficult to regard as a signal close to an original atrial signal. Accordingly, the signal may be an index indicating that atrial fibrillation occurred, but has a limitation in extracting information that may be used as a predictive factor.

SUMMARY

To overcome the foregoing issues, determining an atrial signal including a $T_a$ wave from a surface electrocardiogram signal and extracting an atrial signal in a closest form to an original atrial signal in a non-invasive manner is required.

In one embodiment, a non-invasive system for estimating an atrial signal includes a plurality of sensors to sense a surface electrocardiogram signal, a reference atrial signal generation unit to generate an estimated ventricular signal with respect to a R wave in an electrocardiogram signal from one sensor among the plurality of sensors, and to generate a reference atrial signal by subtracting the estimated ventricular signal from the electrocardiogram signal from the one sensor, and an atrial signal estimation unit to generate an estimated atrial signal by applying a constrained independent component analysis (cICA) algorithm based on the reference atrial signal to the received surface electrocardiogram signal, and to estimate one of the estimated atrial signals as an actual atrial signal.

Alternatively, in one embodiment, the atrial signal estimation unit may apply the constrained independent component analysis algorithm using a negentropy contrast function.

Alternatively, in one embodiment, the atrial signal estimation unit may extract each of a plurality of electrocardiogram signals by applying a constrained independent component analysis algorithm to the received surface electrocardiogram signal, may calculate closeness measures between the plurality of extracted electrocardiogram signals and the reference atrial signal, and may determine an atrial signal of which a calculated closeness measure is optimum, as the estimated atrial signal.

Alternatively, in one embodiment, the atrial signal estimation unit may apply the constrained independent component analysis algorithm iteratively using the estimated atrial signal as an input, and the atrial signal estimation unit may estimate a final estimated atrial signal as the actual atrial signal by executing the constrained independent component analysis algorithm iteratively until the closeness measure is optimized.

Alternatively, in one embodiment, the atrial signal estimation unit may calculate the closeness measure using the Euclidean distance.

Alternatively, in one embodiment, the atrial signal estimation unit may apply the constrained independent component analysis algorithm under a condition that a square of an average for each of the plurality of electrocardiogram signals is equal.

Alternatively, in one embodiment, the reference atrial signal generation unit may generate the estimated ventricular signal using an event synchronized adaptive filter, and the event synchronized adaptive filter may apply an impulse signal synchronized with the R wave to the received surface electrocardiogram signal.

Alternatively, in one embodiment, the electrocardiogram signal from the one sensor among the plurality of sensors may be an electrocardiogram signal from a sensor for a standard lead II or a precordial lead $V_1$.

A non-invasive method for estimating an atrial signal according to an exemplary embodiment includes receiving a surface electrocardiogram signal from a plurality of sensors, generating an estimated ventricular signal with respect to a R wave in an electrocardiogram signal from one sensor among the plurality of sensors, and generating a reference atrial signal by subtracting the estimated ventricular signal from the electrocardiogram signal from the one sensor, and generating estimated atrial signals by applying a constrained independent component analysis (cICA) algorithm based on the reference atrial signal to the received surface electrocardiogram signal, and extracting an atrial signal closest to an original atrial signal from the estimated atrial signal.

Alternatively, in one embodiment, the constrained independent component analysis algorithm may use a negentropy contrast function.

Alternatively, in one embodiment, the estimating as the actual atrial signal may include extracting each of a plurality of electrocardiogram atrial signals by applying a constrained independent component analysis algorithm to the received surface electrocardiogram signal, calculating closeness measures between the plurality of extracted electrocardiogram signals and the reference atrial signal, and determining an electrocardiogram signal of which a calculated closeness measure is optimum, as the estimated atrial signal.

Alternatively, in one embodiment, the estimating as the actual atrial signal may include applying the constrained independent component analysis algorithm iteratively using the estimated atrial signal as an input, and the estimating as the actual atrial signal may include estimating a final atrial signal as the actual atrial signal by executing the constrained independent component analysis algorithm iteratively until the closeness measure is optimized.

Alternatively, in one embodiment, the closeness measure may be calculated using the Euclidean distance method.

Alternatively, in one embodiment, the constrained independent component analysis algorithm may be applied under a condition that a square of an average for each of the plurality of electrocardiogram signals is equal.

Alternatively, in one embodiment, the generating of the reference atrial signal may include generating the estimated ventricular signal using an event synchronized adaptive filter, and the event synchronized adaptive filter may apply an impulse signal synchronized with the R wave to the received surface electrocardiogram signal.

Alternatively, in one embodiment, the electrocardiogram signal from the one sensor among the plurality of sensors may be an electrocardiogram signal from a sensor for a standard lead II or a precordial lead $V_1$.

Alternatively, in one embodiment, the method for estimating an atrial signal may further include generating an estimated ventricular signal with respect to a R wave in an electrocardiogram signal from one sensor among the plurality of sensors, and estimating, as an actual ventricular signal, a ventricular signal before subtracting the estimated ventricular signal from the electrocardiogram signal from the one sensor.

According to an exemplary embodiment, it is possible to estimate an atrial signal closest to an actual atrial signal from a surface electrocardiogram signal using a constrained independent component analysis-based method. The estimated atrial signal may be used as a predictive factor for prediction of an atrium-related disease. Also, by extension, a correlation between an atrial signal and an atrium-related disease is identified and may be widely applied to, for example, management of an atrial fibrillation patient, discovery of a high risk group, evaluation of atrial fibrillation treatment, and the like.

BRIEF DESCRIPTION OF THE DRAWINGS

FIGS. 5A through 5D are graphs illustrating a waveform of an exemplary electrocardiogram signal in each operation of FIG. 4B.

FIG. 8C illustrates an atrial signal estimated by an apparatus or method according to an exemplary embodiment.

DETAILED DESCRIPTION

Figure 1:
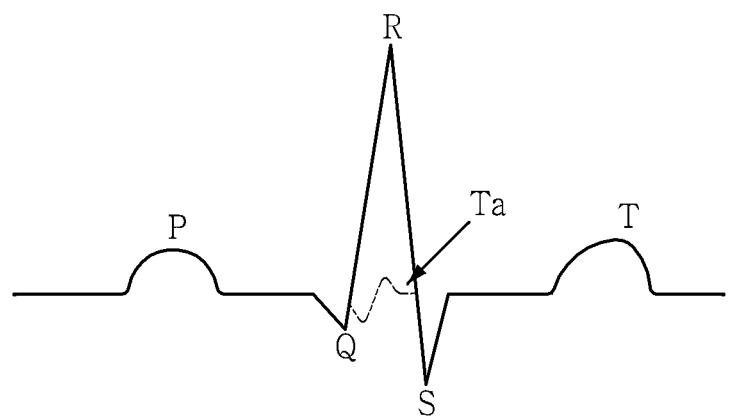
FIG. 1 is a diagram illustrating a typical electrocardiogram waveform.

The terminology used herein is for the purpose of describing particular embodiments only and is not intended to be limiting of the present disclosure. As used herein, the singular forms "a", "an" and "the" are intended to include the plural forms as well, unless the context clearly indicates otherwise. Furthermore, it should be understood that the use of the terms "comprises" and/or "comprising", or "includes" and/or "including" when used in this specification, specify the presence of stated features, integers, steps, operations, elements, components, and/or groups thereof, but do not preclude the presence or addition of one or more other features, integers, operations, elements, components, and/or groups thereof.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein. Like reference numerals presented in the drawings indicate like elements. However, in the description of exemplary embodiments, related known functions or constructions are not described in detail but omitted if they would obscure the general inventive concept with unnecessary detail. Also, in the drawings, the size of some of the elements may be exaggerated and not drawn on scale for illustrative purposes.

The embodiments described herein may take the form of entirely hardware, partially hardware and partially software, or entirely software. The term "unit", "module", "device" or "system" as used herein is intended to refer to a computer-related entity, either hardware, a combination of hardware and software, or software. For example, a unit, module, device or system as used herein can be, but is not limited to being, a process running on a processor, a processor, an object, an executable, a thread of execution, a program, and/or a computer. By way of illustration, both an application running on a computer and the computer can be a unit, module, device or system of the present disclosure.

The embodiments are described with reference to flowcharts presented in the drawings. For concise description, the method is illustrated and described as a series of blocks, but the present disclosure is not limited to an order of the blocks, and some of the blocks may be placed with the other blocks in a different order from an order illustrated and described herein or may be concurrent with the other blocks, and a variety of different branches, flow paths, and block orders achieving a same or similar result may be implemented. Also, for implementation of the method described herein, all the blocks shown herein may not be required. Further, the method according an exemplary embodiment may be implemented in a form of a computer program for performing a series of processes, and the computer program may be recorded in a computer-readable recording medium.

Hereinafter, exemplary embodiments of the present disclosure will be described in detail with reference to the drawings.

Figure 2:
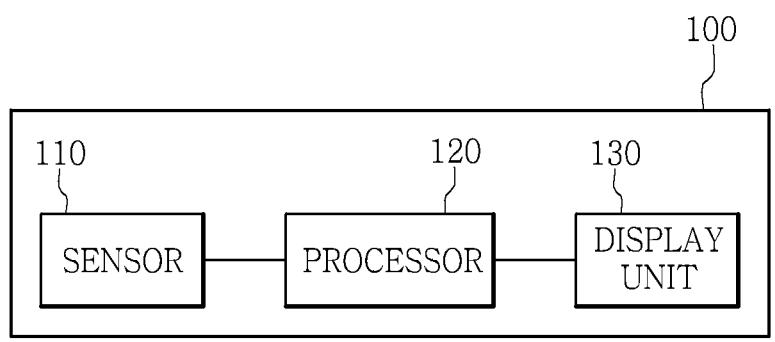
FIG. 2 is a diagram illustrating a construction of a non-invasive system for estimating an atrial signal according to an exemplary embodiment.

FIG. 2 is a diagram illustrating a construction of a non-invasive system for estimating an atrial signal according to an exemplary embodiment. Referring to FIG. 2, the non-invasive system 100 for estimating an atrial signal according to an exemplary embodiment may include a sensor 110, a processor 120, and a display unit 130.

The sensor 110 is any device that is attached to a body of a patient on which an electrocardiogram test is to be performed, to sense a surface electrocardiogram signal. For example, the sensor 110 may comprise a plurality of electrodes, and is attached around a heart of a patient to measure an electrocardiogram signal non-invasively. In case in which a plurality of leads is used, a plurality of electrocardiogram signals is measured at different locations.

Figure 3A:
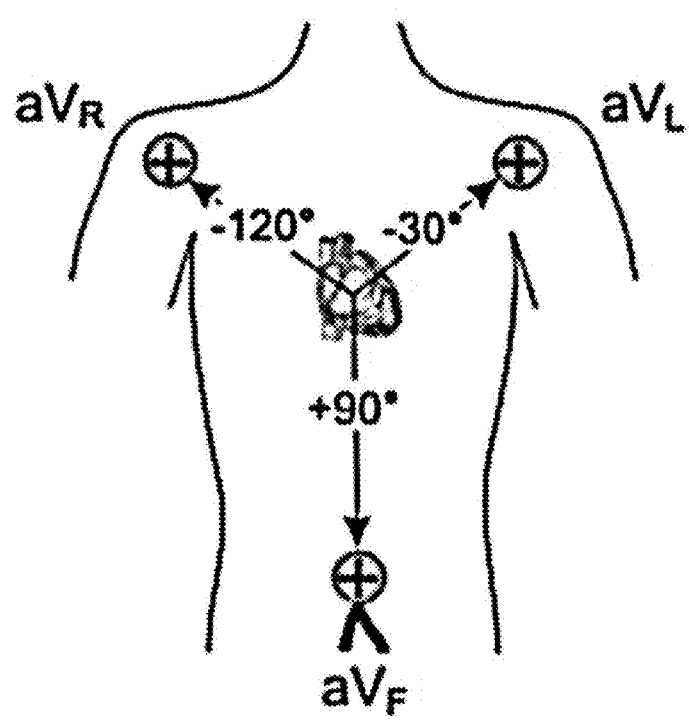
FIGS. 3A and 3B are diagrams illustrating a location of an electrocardiogram signal to be sensed according to an exemplary embodiment.
Figure 3A:
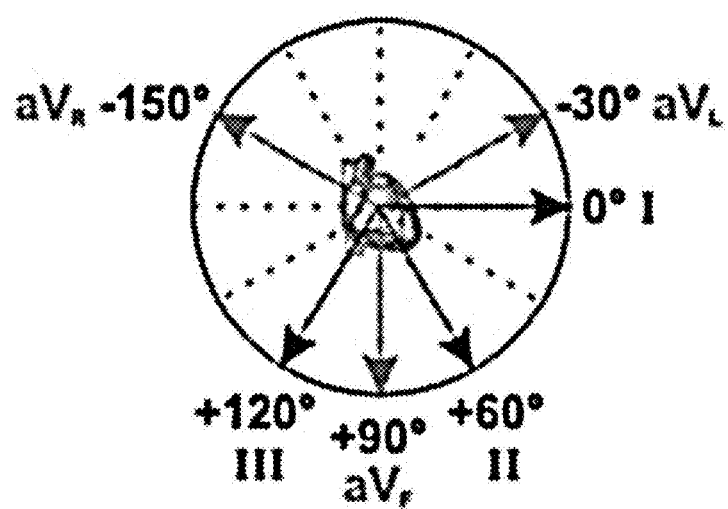
Figure 3B:
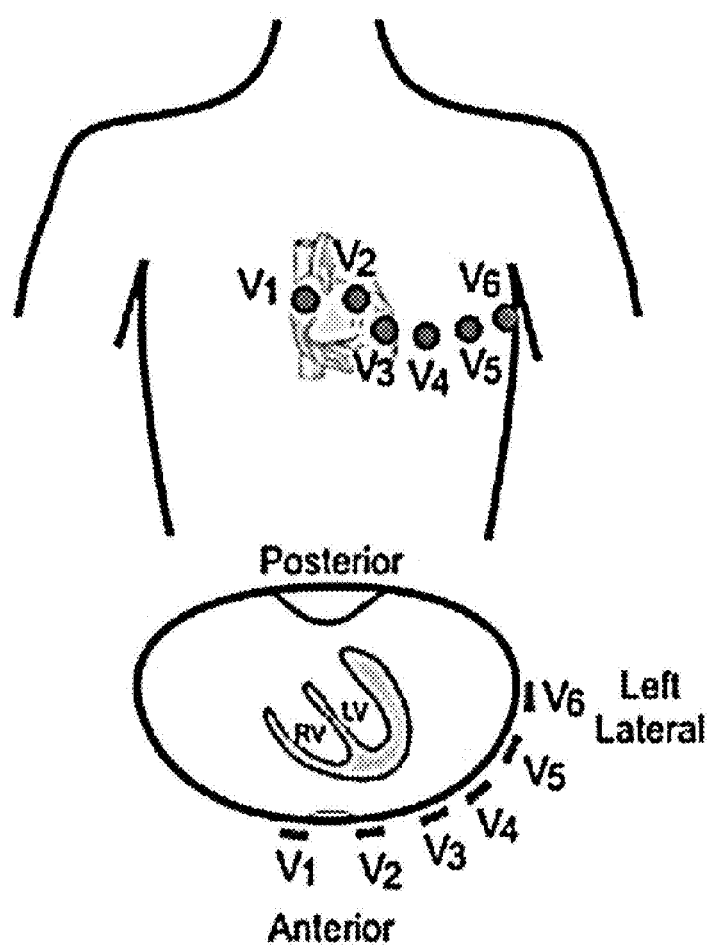

FIGS. 3A and 3B are diagrams illustrating a location of an electrocardiogram signal to be sensed according to an exemplary embodiment.

FIG. 3A illustrates an extremity lead and a standard lead, and FIG. 3B illustrates a precordial lead. The extremity lead records an electrocardiogram by unipolar induction by connecting electrodes to a right hand, a left hand, and a left foot, and a part to which the electrode is attached functions as a cathode. Because an electrocardiogram waveform recorded by a unipolar extremity lead is small, aVR, aVL, and aVF ('a' stands for 'augmented') formed by augmenting an electrocardiogram waveform by 50% are clinically used. The standard lead records an electrocardiogram by bipolar induction by connecting electrodes to a right hand, a left hand, and a left foot, and an electrode connected to a right foot functions as a ground. Here, a lead II is recorded by a potential difference between a right hand and a left foot. Also, the precordial lead is a way of recording an electrocardiogram at a part close to a heart, and $V_1$ and $V_2$ are located at a part of a right ventricle, $V_3$ and $V_4$ at a part of an interventricular septum, and $V_5$ and $V_6$ at a part of a left ventricle.

Because an atrial signal is measured most strongly in the standard lead II and the precordial lead $V_1$ among the above leads, at least one sensor among a plurality of sensors for electrocardiogram measurement may be attached to the standard lead II and the precordial lead $V_1$, and may sense an electrocardiogram signal.

The processor 120 may estimate an atrial signal by analyzing a surface electrocardiogram signal received from the sensor 110. For example, the processor 120 may be any central processing unit (CPU) having an information processing function. For a simplified description, a surface electrocardiogram signal will be hereinafter referred to as an electrocardiogram signal.

In one embodiment, the processor 120 may include a reference atrial signal generation unit and an atrial signal estimation unit.

The display unit 130 may be any display equipment that may visually display an atrial signal estimated by the processor 120, for example, liquid crystal display (LCD), organic light-emitting diode (OLED), plasma display panel (PDP), and LED devices.

Hereinafter, a function of the processor 120 estimating a necessary atrial signal by analyzing an electrocardiogram signal received from the sensor 110 will be described in detail.

Figure 4A:
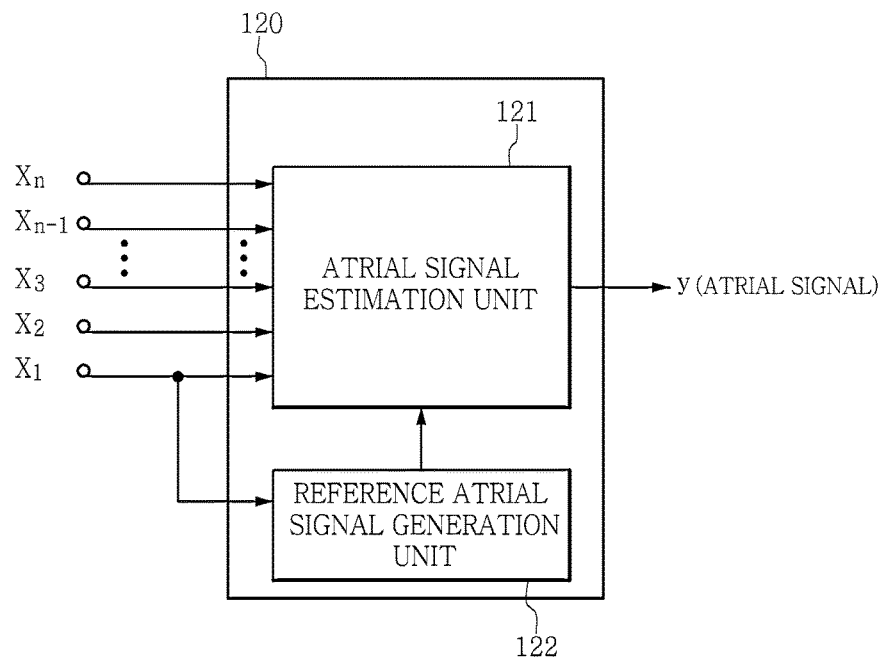
FIG. 4A is a diagram illustrating a function of a system for estimating an atrial signal according to an exemplary embodiment.

FIG. 4A is a diagram illustrating a function of a system for estimating an atrial signal according to an exemplary embodiment. Referring to FIG. 4A, the processor 120 includes an atrial signal estimation unit 121 and a reference atrial signal generation unit 122.

Also, a plurality of electrocardiogram signals $x_1$-$x_n$, from a plurality of sensors is input to the atrial signal estimation unit 121, and among the plurality of electrocardiogram signals, at least one electrocardiogram signal (for example, $x_1$) is input to the reference atrial signal generation unit 122.

The reference atrial signal generation unit 122 may provide a reference atrial signal to the atrial signal estimation unit 121 by preprocessing the input electrocardiogram signal. The atrial signal estimation unit 121 may estimate an atrial signal based on the plurality of electrocardiogram signals and the reference atrial signal, and may output the estimated atrial signal. The output atrial signal y may be transmitted to the display unit 130.

Figure 4B:
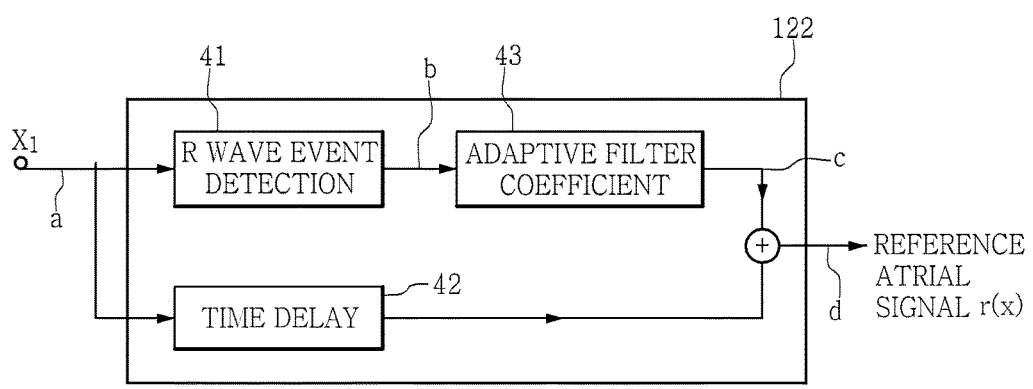
FIG. 4B is a diagram illustrating a function of a reference atrial signal generation unit (122) according to an exemplary embodiment.

FIG. 4B is a diagram illustrating a function of the reference atrial signal generation unit 122 according to an exemplary embodiment. As described in the foregoing, at least one electrocardiogram signal among the plurality of electrocardiogram signals may be input to the reference atrial signal generation unit 122, and preferably, one electrocardiogram signal may be input. Also, the input electrocardiogram signal may be an electrocardiogram signal in a standard lead II or a precordial lead $V_1$.

The reference atrial signal generation unit 122 may generate an estimated ventricular signal with respect to a R wave in an electrocardiogram signal from one sensor (for example, electrode) among the plurality of sensors, and may generate a reference atrial signal by subtracting the estimated ventricular signal from the electrocardiogram signal from the one sensor.

As the reference atrial signal outputted from the reference atrial signal generation unit 122 has a higher correlation with an original atrial signal, an estimated atrial signal may be closer to an actual atrial signal. Accordingly, the reference atrial signal generation unit 122 extracts a reference atrial signal by applying an event synchronized adaptive filter (ESAF) to a single-lead electrocardiogram signal (for example, II or $V_1$) in which an atrial signal is measured most strongly in a multi-lead electrocardiogram.

Specifically, the reference atrial signal generation unit 122 may use the following Equations 1 though 3 to generate an estimated ventricular signal.

$$c(t) = \begin{cases} 1 & (t = t_R) \\ 0 & (t \neq t_R) \end{cases} \quad \text{[Equation 1]}$$

$$x_v(t) = \begin{cases} \sum_{i=t_Q}^{t_T} h(t) \cdot c(t-i) & (t_Q \leq t \leq t_T) \\ 0 & (1 \leq t < t_Q, t_T < t < t_Q, t_T < t \leq T) \end{cases} \quad \text{[Equation 2]}$$

$$r(t) = x_1(t) - x_v(t) \quad \text{[Equation 3]}$$

In the above equations, t denotes time, $t_R$ denotes a time (location) at which a R wave occurs in an electrocardiogram signal, and $t_Q$ and $t_T$ denote a time at which a Q wave occurs and a time at which a T wave occurs, respectively. Also, c(t) denotes an impulse sequence signal synchronized with an event of a QRST waveform, $x_1(t)$ denotes an electrocardiogram signal measured from any one sensor among a plurality of sensors, $x_v(t)$ denotes an estimated ventricular signal, and r(t) denotes a reference atrial signal. Also, a coefficient h(t) of an adaptive filter is learned using a least-mean-squares (LMS) algorithm, and an estimated ventricular signal is outputted at an output end of the adaptive filter (that is, a result of Equation 2), and finally, a reference atrial signal is outputted (that is, a result of Equation 3).

Here, the reference atrial signal generation unit 122 may obtain a length of a QRST waveform (L=$t_T$-$t_Q$+1 where $t_T$ and $t_Q$ denote locations of a Q wave and a T wave, respectively) and a location ($t_R$) of a R wave through a Pan-Tompkins algorithm for QRST wave detection being generally widely used.

Referring to FIG. 4B, a R wave event for the received electrocardiogram signal is detected (41), and for the detected R wave event, an estimated ventricular signal $x_v(t)$ is outputted through an adaptive filter 43. Also, $x_v(t)$ is time-delayed (42) so that a reference atrial signal r(t) may be outputted by subtracting $x_v(t)$ from $x_1(t)$ at the same time.

FIGS. 5A through 5D are graphs illustrating a waveform of an exemplary electrocardiogram signal in each operation of FIG. 4B. Identification symbols 'a' through 'd' in each operation of FIG. 4B correspond to FIGS. 5A through 5D, respectively.

Figure 5A:
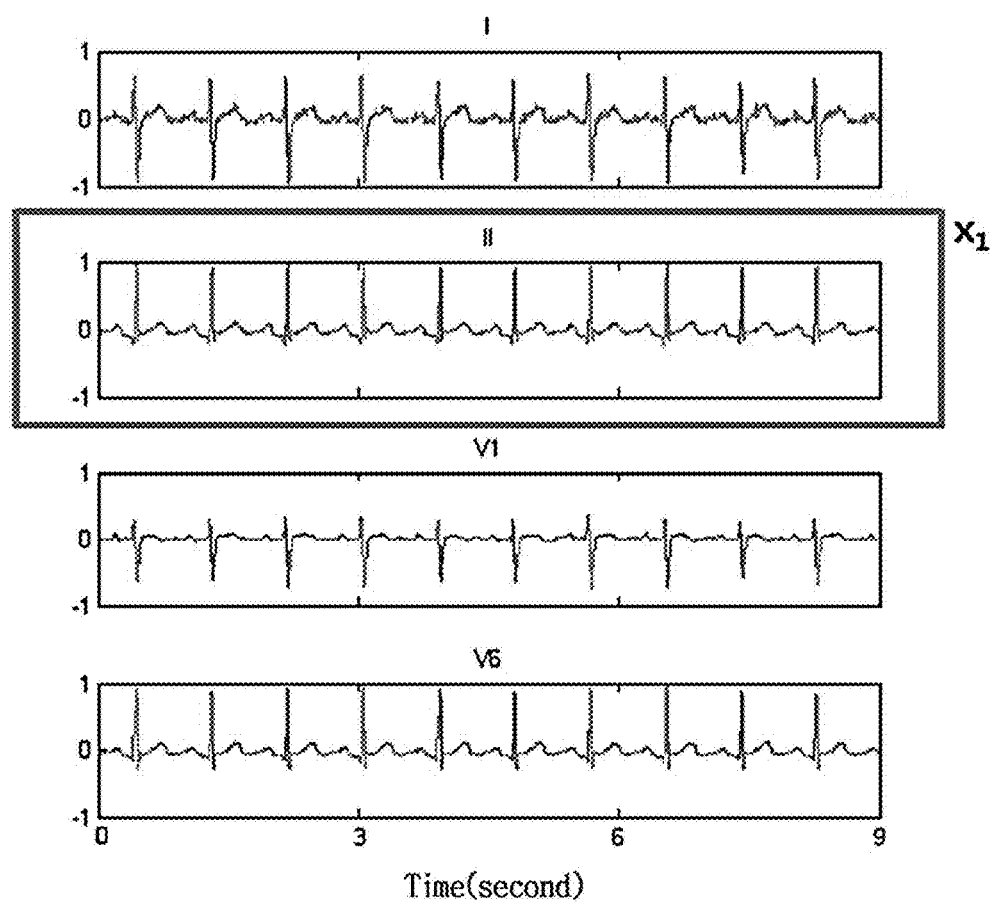
Figure 5C:
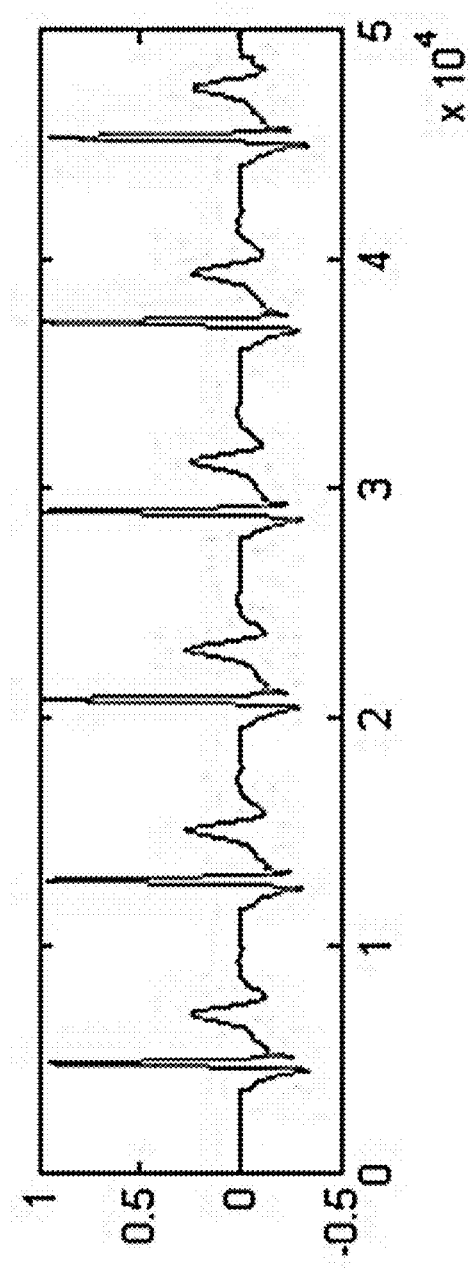
Figure 5D:
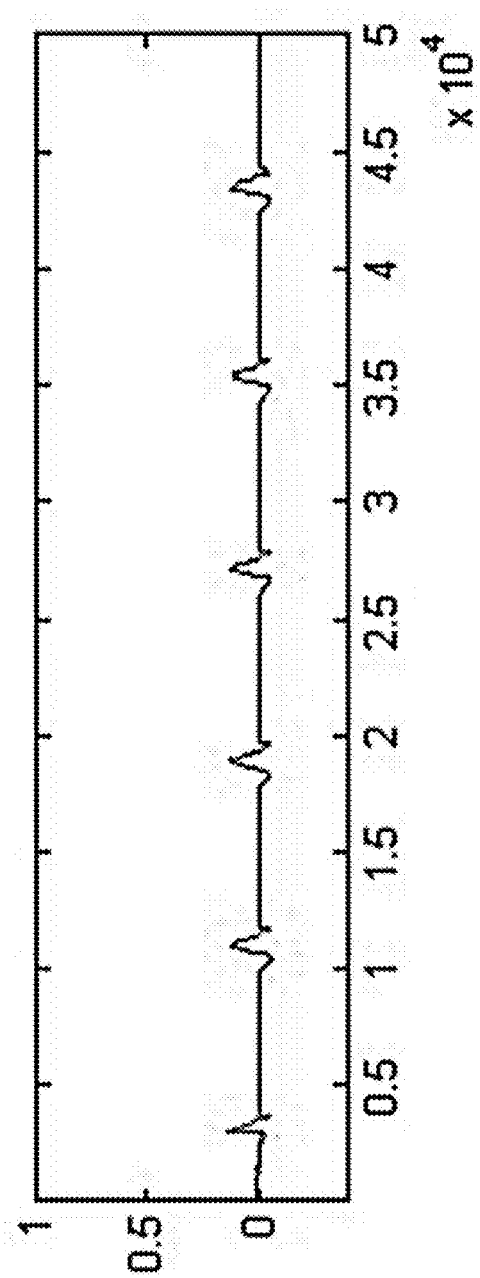

FIG. 5A illustrates an electrocardiogram signal (here, $x_1$ indicated as a box) measured from any one electrode input to the reference atrial signal generation unit 122 among a plurality of electrocardiogram signals. FIG. 5B illustrates an electrocardiogram signal in which a R wave event is detected, FIG. 5C illustrates an estimated ventricular signal $x_v(t)$ having passed through an even synchronized adaptive filter, and FIG. 5D illustrates a reference atrial signal obtained by subtracting $x_v$ from $x_1$.

As described in the foregoing, the reference atrial signal generation unit 122 may generate a reference atrial signal based on a surface electrocardiogram signal measured from one sensor, and provide it to the atrial signal estimation unit 121.

The atrial signal estimation unit 121 may extract an atrial signal closest to an original atrial signal by applying a constrained independent component analysis (cICA) algorithm based on the received reference atrial signal and the received surface electrocardiogram signal.

In case in which a general independent component analysis algorithm is used, the shortcoming is that it is impossible to understand what each separated signal represents and comparison of each signal is not easy due to different scales for each separated signal. That is, according to a general independent component analysis algorithm, there are problems that identifying an atrial signal among each output signal must rely on an intuitive decision by a physician and very different sizes of each output signal hamper a physician's making an intuitive decision.

The atrial signal estimation unit 121 according to the embodiment performs an optimization process iteratively until to satisfy a predetermined convergence threshold so that an output of the constrained independent component analysis algorithm to which the reference atrial signal is applied is estimated as a signal closest to an atrial signal. The convergence threshold may be determined based on a closeness measure obtained from the output estimated atrial signal and the reference atrial signal.

For example, the atrial signal estimation unit 121 estimates an atrial signal by including the following procedure in the process of extracting each of the plurality of electrocardiogram signals by applying the independent component analysis algorithm to the received surface electrocardiogram signal. The atrial signal estimation unit 121 first may set differences between the plurality of extracted electrocardiogram signals and the reference atrial signal as closeness measures, and may determine an electrocardiogram signal of which a calculated closeness measure is optimum as the estimated atrial signal. When the atrial signal estimation unit 121 performs the foregoing process iteratively until to find an optimum unmixing vector, the atrial signal estimation unit 121 may finally estimate as an actual atrial signal.

Hereinafter, a description of a specific operation of the atrial signal estimation unit 121 will be provided.

The atrial signal estimation unit 121 needs to calculate an unmixing vector w to extract only signals closest to a desired atrial signal from an electrocardiogram signal obtained through a plurality of electrodes, and for this, uses a reference atrial signal extracted through an event synchronized adaptive filter.

First, a linear model of M mixed independent source signals s(t) (here, t=1,2, . . . T, and T denotes a length of a signal) measured through N channels in a noiseless environment is given by the following Equation 4.

$$x(t)=A\cdot s(t) \quad \text{[Equation 4]}$$

where A denotes a mixing matrix having a size of N×M, and x(t) denotes signals mixed by the mixing matrix, that is, signals measured from sensors. General independent component analysis aims to find an M×N unmixing matrix W of Equation 5 able to separate s(t) representing M signals closest to a source signal.

$$\hat{s}(t)=Wx(t) \quad \text{[Equation 5]}$$

The atrial signal estimation unit 121 may apply an independent component analysis algorithm using a negentropy contrast function as a method for generating an estimated atrial signal. For this, an assumption is that a negentropy contrast function for estimating a source signal has M optimization solutions $w_i$ (i=1,2, . . . ,M), and additionally, a closeness measure between an estimated atrial signal $y(t)=w_M^T x(t)$ (here, y(t) denotes an M-th element to find using constrained independent component analysis among s(t)) and a reference atrial signal is defined and applied as ε(y(t), r(t)).

The estimated atrial signal y(t) is an atrial signal outputted by the constrained independent component analysis algorithm according to an exemplary embodiment, and by inputting the estimated atrial signal y(t) to the constrained independent component analysis algorithm as an input again, an optimization process is performed iteratively, and based on this iteration, an estimated atrial signal outputted at a proper level may be estimated as an actual atrial signal. The atrial signal estimation unit 121 may calculate the closeness measure using the Euclidean distance.

Also, when the linearly mixed source signals measured are x(t), Equation 6 is satisfied.

$$\varepsilon(w^{*T}x(t),r(t))<\varepsilon(w_1^T x(t),r(t))\leq \ldots \leq \varepsilon(w_{M-1}^T x(t),r(t)) \quad \text{[Equation 6]}$$

where w* denotes an optimum unmixing vector of an unmixing vector $w_M$, and $w_j$(j=1,2, . . . M−1) denotes optimum unmixing vectors for unwanted remaining signals. Also, a threshold ξ for limiting a number of iterations of an optimization process and extracting an atrial signal from an electrocardiogram signal may be defined as Equation 7.

$$\xi \in [\varepsilon(w^{*T}x(T),r(t)),\varepsilon(w_1^T x(t),r(t))) \quad \text{[Equation 7]}$$

In this instance, an inequality constraint for finding an optimization solution $y(t)=w^{*T}x(t)$ is given by Equation 8.

$$e(w)=\varepsilon(y(t),r(t))-\xi \leq 0 \quad \text{[Equation 8]}$$

When Equation 8 is used as a constraint together with a negenstropy contrast function which is an objective function, an optimization formula for obtaining a desired output may be represented by Equation 9.

$$\text{maximize } J(y) \propto [E\{G(y(t))\}-E\{(v(t))\}]^2$$

$$\text{subject to } e(w)\leq 0, f(w)=E(y(t))^2-1=0 \quad \text{[Equation 9]}$$

where E denotes an average, G denotes a nonquadratic function, v(t) denotes a zero mean, f(w) denotes an equality constraint to limit an output to have unit variance, and J(y) denotes an objective function to be optimized in a constrained independent component analysis algorithm. That is, only a desired signal (atrial signal) may be extracted by the inequality constraint, and scales of output signals may be unified by the equality constraint.

However, it is not easy to find a correct threshold for convergence of an optimization algorithm, and thus, the atrial signal estimation unit 121 according to an exemplary embodiment may use Equation 10 in which an optimization method for calculating a maximum value of a closeness measure is applied to Equation 9 conversely instead of finding a proper threshold.

$$\text{maximize } J(w) \propto [E\{G(y(t))\}-E\{G(v(t))\}]^2$$

$$K(w)=\varepsilon(y(t),r(t))$$

$$\text{subject to } f(w)=E(y(t))^2-1=0 \quad \text{[Equation 10]}$$

In Equation 10, optimization methods for calculating maximum values of J(w) and K(w) are alternately applied under an equality constraint rather than an inequality constraint similar to Equation 9. Here, J(w) and K(w) are objective functions to be optimized in a constrained independent component analysis algorithm.

Also, in case in which an impulse signal is used as a reference signal, convergence of a constrained independent component analysis algorithm may not be guaranteed due to a problem of being different from a source signal, and in case in which a signal having a same sampling frequency is mixed, or in a situation in which a sampling frequency changes according to circumstances, application is impossible, and thus, the atrial signal estimation unit 121 uses a reference atrial signal outputted by applying an event synchronized adaptive filter as described in the foregoing.

Figure 6:
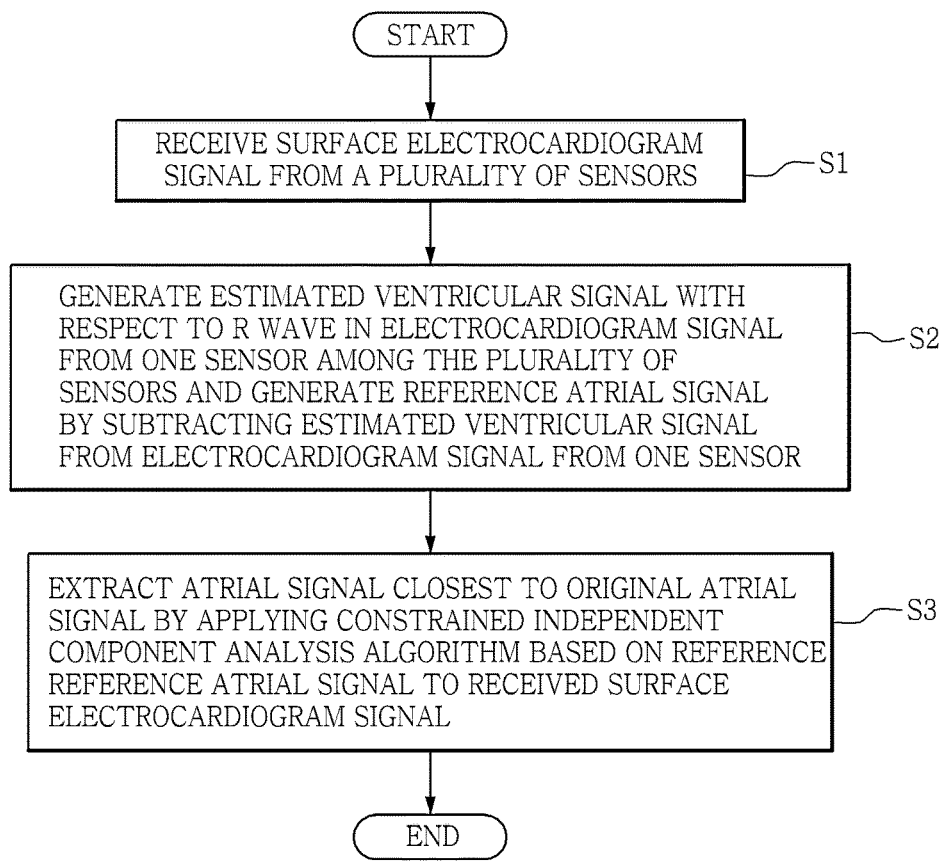
FIG. 6 is a flowchart illustrating a non-invasive method for estimating an atrial signal according to an exemplary embodiment.

FIG. 6 is a flowchart illustrating a non-invasive method for estimating an atrial signal according to an exemplary embodiment. Referring to FIG. 6, the non-invasive method for estimating an atrial signal includes receiving a surface electrocardiogram signal from a plurality of sensors (S1), generating an estimated ventricular signal with respect to a R wave in an electrocardiogram signal from one sensor among the plurality of sensors and generating a reference atrial signal by subtracting the estimated ventricular signal from the electrocardiogram signal from the one sensor (S2), and extracting an atrial signal closest to an original atrial signal by applying a constrained independent component analysis algorithm based on the reference atrial signal to the received surface electrocardiogram signal (S3).

In one embodiment, an objective function for use in the constrained independent component analysis algorithm may use a negentropy contrast function.

Also, the estimating as the actual atrial signal (S3) may include extracting each of a plurality of electrocardiogram atrial signals by applying a constrained independent component analysis algorithm to the received surface electrocardiogram signal, calculating closeness measures between the plurality of extracted electrocardiogram signals and the reference atrial signal, and determining an atrial signal of which a closeness measure is optimum, as the estimated atrial signal.

Also, the estimating as the actual atrial signal (S3) may estimate a final atrial signal as the actual atrial signal by applying the constrained independent component analysis algorithm iteratively using the estimated atrial signal as an input, and in this instance, the constrained independent component analysis algorithm is executed iteratively until the closeness measure is optimized.

Also, the closeness measure may be calculated using a means such as the Euclidean distance or the like, and the constrained independent component analysis algorithm may be applied under a condition that a square of an average for each of the plurality of electrocardiogram signals is equal.

Also, the generating of the reference atrial signal (S2) may generate the estimated ventricular signal using an event synchronized adaptive filter, and in this instance, the event synchronized adaptive filter may apply an impulse signal synchronized with the R wave to the received surface electrocardiogram signal. Also, the electrocardiogram signal from one sensor among the plurality of sensors may be an electrocardiogram signal from a sensor for a standard lead II or a precordial lead $V_1$.

Also, the non-invasive method for estimating an atrial signal according to an exemplary embodiment may further include generating an estimated ventricular signal with respect to a R wave in an electrocardiogram signal from one sensor among the plurality of sensors, and estimating, as an actual ventricular signal, a ventricular signal before subtracting the estimated ventricular signal from the electrocardiogram signal from the one sensor.

The non-invasive method for estimating an atrial signal may be supplemented by referring to the description of the non-invasive system for estimating an atrial signal described in the foregoing, and may be performed by the non-invasive system for estimating an atrial signal.

Figure 7A:
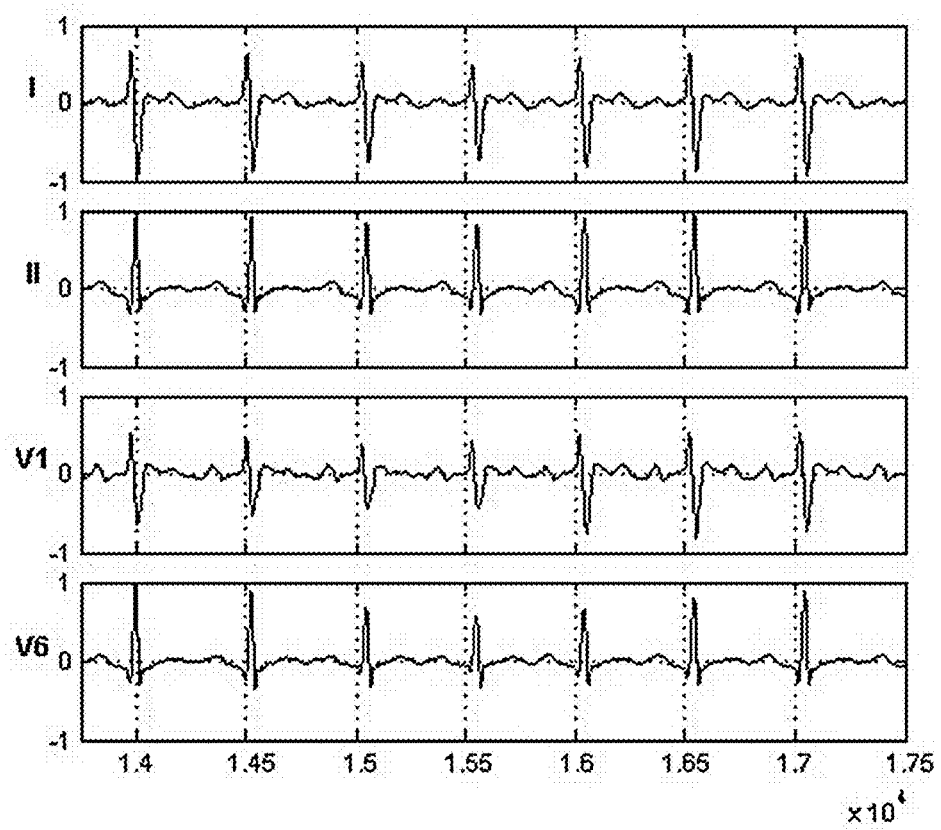
FIGS. 7A and 7B are graphs illustrating an atrial signal estimated by a non-invasive system or method for estimating an atrial signal according to an exemplary embodiment.
Figure 7B:
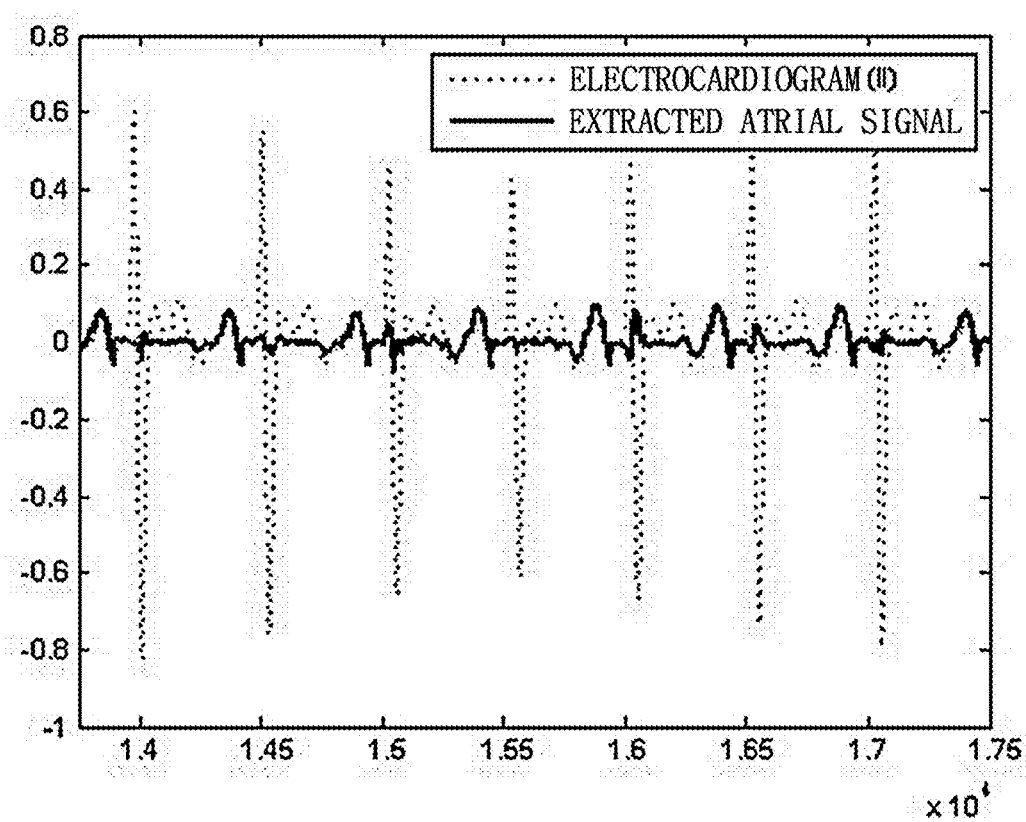

FIGS. 7A and 7B are graphs illustrating an atrial signal estimated by the non-invasive system or method for estimating an atrial signal according to an exemplary embodiment. FIG. 7A illustrates surface electrocardiograms measured in standard leads I and II and precordial leads $V_1$ and $V_6$, and FIG. 7B illustrates an electrocardiogram signal and an estimated atrial signal.

In the graphs of FIGS. 7A and 7B, an x-axis unit is msec and a y-axis unit is voltage. A surface electrocardiogram was measured at a rate of 2,000 Hz. In FIG. 7B, an electrocardiogram in a precordial lead $V_1$ is indicated by a dotted line, and an estimated atrial signal is indicated by a thick solid line. Referring to FIG. 7B, it was found that an atrial signal including P and $T_a$ was extracted.

Figure 8A:
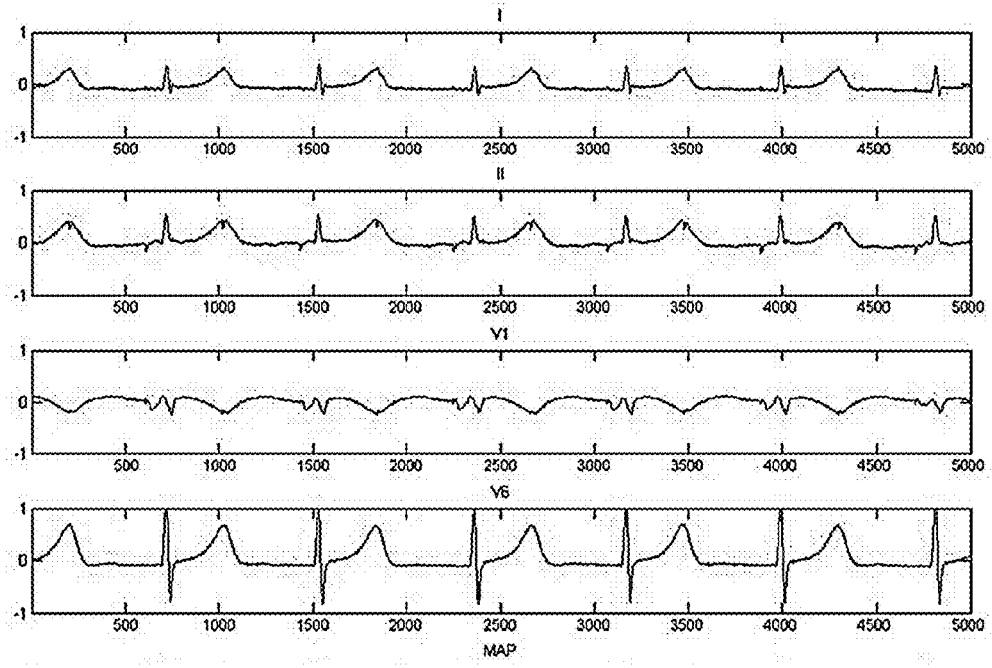
FIG. 8A illustrates electrocardiogram measurement results for standard leads I and II and precordial leads $V_1$ and $V_6$.
Figure 8B:
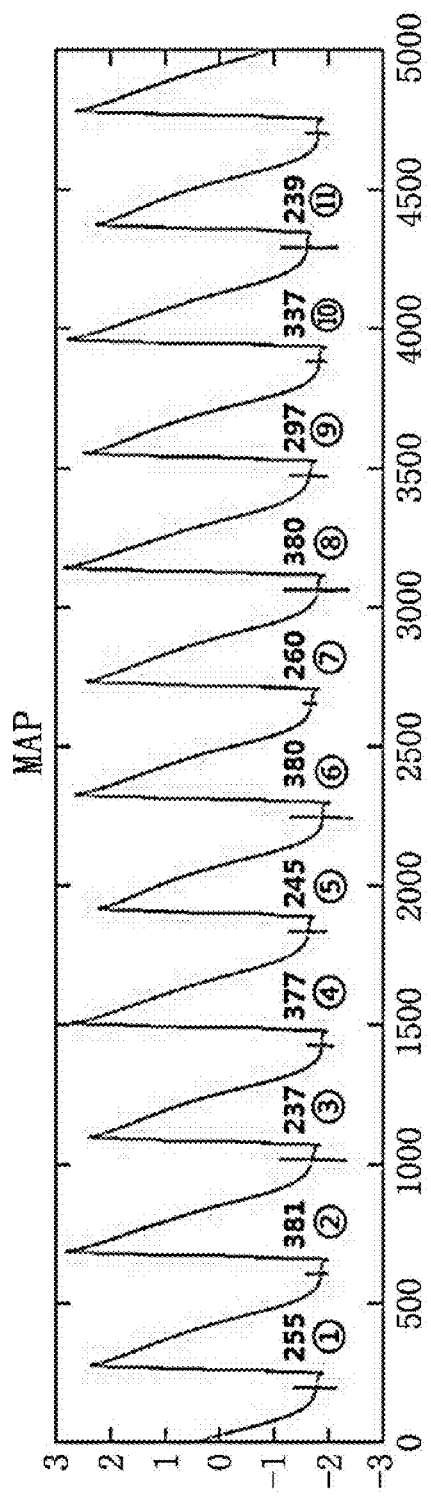
FIG. 8B illustrates a monophasic action potential signal.

FIG. 8A illustrates electrocardiogram measurement results for standard leads I and II and precordial leads $V_1$ and $V_6$, FIG. 8B illustrates a monophasic action potential signal, and FIG. 8C illustrates an atrial signal estimated by an apparatus or method according to an exemplary embodiment.

FIG. 8A shows a surface electrocardiogram signal (I, II, $V_1$, $V_6$) measured at 2,000 Hz with atrial pacing at 400 msec in an atrial fibrillation patient who completed an atrial fibrillation operation by an electrical catheter ablation to observe alternation of a $T_a$ wave in a separated signal. FIG. 8B is measured under the same condition as FIG. 8A, and shows a monophasic action potential acquired from an electrical conductor invasively inserted into an atrium by an electrical catheter ablation. FIG. 8C shows an atrial signal estimated by extracting a reference atrial signal from the electrocardiogram signal in $V_1$ of FIG. 8B according to an exemplary embodiment. In FIGS. 8A through 8C, an x-axis unit is msec and a y-axis unit is voltage.

In the graph of FIG. 8B, it was found that odd numbered (①③⑤⑦⑨) durations (237-297 msec) were relatively short and even numbered (②④⑥⑧⑩) durations (337-381 msec) were long, and alternation was seen. The alternation of atrial monophasic action potential durations and the alternation of ventricular monophasic action potential durations are related to atrial fibrillation and ventricular fibrillation, respectively.

In the graph of FIG. 8C, a $T_a$ wave is represented by a dotted circle. In the drawing, it was found that waveforms of odd numbered (①③⑤⑦⑨) $T_a$ waves were relatively flat and waveforms of even numbered (②④⑥⑧⑩) $T_a$ waves were relatively downward convex, and alternation was seen. Therefore, according to an exemplary embodiment, atrial fibrillation may be diagnosed and predicted by estimating an atrial signal representing a $T_a$ wave.

The system and method for estimating an atrial signal described in the foregoing may be manufactured as a hardware device, or may be added and applied in a software form to an existing equipment for ventricular signal diagnosis. Also, the system and method for estimating an atrial signal may be used in a mobile device equipped with an electrocardiogram sensing system.

While the foregoing has been described with reference to the embodiments shown in the drawings, this is for illustration only, and it will be understood by those skilled in the art that various changes in form and details may be made thereto. However, such changes are construed as falling within the spirit and scope of the present disclosure. Therefore, the scope of the present disclosure shall be defined by the spirit of the appended claims.

What is claimed is:

1. An apparatus to estimate an atrial signal, comprising:
 a lead;
 sensors configured to sense electrocardiogram signals;
 a processor in communication with the sensors, the processor comprising:
  a reference atrial signal generator configured to generate an estimated ventricular signal with respect to an R wave in an electrocardiogram signal among the electrocardiogram signals from a sensor among the sensors which is attached to the lead, and to generate a reference atrial signal by subtracting the estimated ventricular signal from the electrocardiogram signal from the sensor; and
  an atrial signal estimator configured to generate an estimated atrial signal by iteratively applying a constrained independent component analysis (cICA) algorithm based on the reference atrial signal to the sensed electrocardiogram signal for a number of iterations; and
 a display in communication with the processor and configured to display a representation of the estimated atrial signal,
 wherein the lead comprises a standard lead II configured to record a potential difference between a right hand and a left foot, or a precordial lead $V_1$ configured to be positioned at a location proximate a heart,
 wherein the atrial signal estimator is further configured to set differences between a plurality of sensed electrocardiogram signals and the reference atrial signal as closeness measures, and determine an electrocardiogram signal of which a calculated closeness measure is maximum as the estimated atrial signal, and
 wherein the maximum of the closeness measure is calculated by a formula according to:

$$\text{maximize } J(w) \propto [E\{G(y(t))\} - E\{G(v(t))\}]^2$$

$$K(w) = \varepsilon(y(t), r(t))$$

subject to $f(w)=E(y(t))^2-1=0$ where E is an average, G is a nonquadratic function, v(t) is a zero mean, y(t) is the estimated atrial signal, r(t) is the reference atrial signal, ε is the closeness measures, f(w) is an equality constraint to limit an output to have unit variance, and J(w) and K(w) are objective functions to be optimized.

2. The apparatus to estimate the atrial signal according to claim 1, wherein the atrial signal estimator is further configured to apply the constrained independent component analysis algorithm using a negentropy contrast function.

3. The apparatus to estimate the atrial signal according to claim 1, wherein the atrial signal estimator is further configured to determine an atrial signal of a calculated closeness measure, as the estimated atrial signal.

4. The apparatus to estimate the atrial signal according to claim 3, wherein the atrial signal estimator is further configured to calculate the closeness measure using an Euclidean distance.

5. The apparatus to estimate the atrial signal according to claim 4, wherein the atrial signal estimator is further configured to apply the constrained independent component analysis algorithm under an equality constraint for a square of an average for each of the electrocardiogram signals.

6. The apparatus to estimate the atrial signal according to claim 1, wherein the reference atrial signal generator is further configured to generate the estimated ventricular signal using an event synchronized adaptive filter, and
wherein the event synchronized adaptive filter is further configured to apply an impulse signal synchronized with the R wave to the received electrocardiogram signal.

7. The apparatus to estimate the atrial signal according to claim 1, wherein the electrocardiogram signal further comprises a $T_a$ wave, and wherein the actual atrial signal is extracted based on the $T_a$ wave of the electrocardiogram signal.

8. A method to estimate an atrial signal, executed by a processor, the method comprising:
sensing an electrocardiogram signal from sensors in communication with the processor;
generating, by a reference atrial signal generator of the processor, an estimated ventricular signal with respect to an R wave in an electrocardiogram signal among the electrocardiogram signals from a sensor among the sensors which is attached to a lead, and generating a reference atrial signal by subtracting the estimated ventricular signal from the electrocardiogram signal from the sensor;
iteratively generating, by an atrial signal estimator of the processor, estimated atrial signals by applying a constrained independent component analysis (cICA) algorithm based on the reference atrial signal to the sensed electrocardiogram signal for a number of iterations, and extracting an actual atrial signal closest to an original atrial signal from the estimated atrial signal; and
displaying a representation of the estimated atrial signal on a display in communication with the processor,
wherein the lead comprises a standard lead II configured to record a potential difference between a right hand and a left food, or a precordial lead $V_1$ configured to be positioned at a location proximate a heart,
wherein the atrial signal estimator is configured to set differences between a plurality of sensed electrocardiogram signals and the reference atrial signal as closeness measures, and determine an electrocardiogram signal of which a calculated closeness measure is maximum as the estimated atrial signal, and
wherein the maximum of the closeness measure is calculated by an formula according to:

maximize $J(w) \propto [E\{G(y(t))\}-E\{G(v(t))\}]^2$ $K(w)=\varepsilon(y(t), r(t))$ subject to $f(w)=E(y(t))^2-1=0$ where E is an average, G is a nonquadratic function, v(t) is a zero mean, y(t) is the estimated atrial signal, r(t) is the reference atrial signal, ε is the closeness measures, f(w) is an equality constraint to limit an output to have unit variance, and J(w) and K(w) are objective functions to be optimized.

9. The method to estimate the atrial signal according to claim 8, wherein the constrained independent component analysis algorithm uses a negentropy contrast function.

10. The method to estimate the atrial signal according to claim 8, wherein the estimating of the actual atrial signal further comprises extracting electrocardiogram atrial signals among the electrocardiogram signals by applying the constrained independent component analysis algorithm to the electrocardiogram signal.

11. The method to estimate the atrial signal according to claim 10, wherein the closeness measure is calculated using an Euclidean distance method.

12. The method to estimate the atrial signal according to claim 11, wherein the constrained independent component analysis algorithm is applied under an equality constraint for a square of an average for each of the plurality of electrocardiogram signals.

13. The method to estimate the atrial signal according to claim 8, wherein the generating of the reference atrial signal further comprises generating the estimated ventricular signal using an event synchronized adaptive filter, and
the event synchronized adaptive filter is configured to apply an impulse signal synchronized with the R wave to the sensed electrocardiogram signal.

14. The method to estimate the atrial signal according to claim 8, wherein the generating of the estimated ventricular signal occurs before the subtracting of the estimated ventricular signal from the electrocardiogram signal.

15. The method to estimate the atrial signal according to claim 8, wherein the electrocardiogram signal further comprises a $T_a$ wave.

16. The method to estimate the atrial signal according to claim 15, further comprising extracting the actual atrial signal based on the $T_a$ wave of the electrocardiogram signal.

17. An apparatus to estimate an atrial signal, comprising:
a lead;
sensors configured to sense electrocardiogram signals;
a processor in communication with the sensors, the processor comprising:
a reference atrial signal generator configured to generate an estimated ventricular signal with respect to an R wave in an electrocardiogram signal among the electrocardiogram signals from a sensor among the sensors which is attached to the lead, and to generate a reference atrial signal by subtracting the estimated ventricular signal from the electrocardiogram signal from the sensor; and
an atrial signal estimator configured to generate an estimated atrial signal by iteratively applying a constrained independent component analysis (cICA)

algorithm based on the reference atrial signal to the sensed electrocardiogram signal for a number of iterations; and a display in communication with the processor and configured to display a representation of the estimated atrial signal, wherein the lead comprises a standard lead II configured to record a potential difference between a right hand and a left food, or a precordial lead $V_1$ configured to be positioned at a location proximate a heart, wherein the atrial signal estimator is further configured to set differences between a plurality of sensed electrocardiogram signals and the reference atrial signal as closeness measures, and determine an electrocardiogram signal of which a calculated closeness measure is maximum as the estimated atrial signal, and wherein the maximum of the closeness measure is calculated by an formula according to:

$$\text{maximize } J(w) \propto [E\{G(y(t))\} - E\{G(v(t))\}]^2$$

$$K(w) = \varepsilon(y(t), r(t))$$

$$\text{subject to } f(w) = E(y(t))^2 - 1 = 0$$

where E is an average, G is a nonquadratic function, v(t) is a zero mean, y(t) is the estimated atrial signal, r(t) is the reference atrial signal, $\varepsilon$ is the closeness measures, the f(w) is an equality constraint to limit an output to have unit variance, and J(w) and K(w) are objective functions to be optimized.

18. A non-transitory computer-readable medium storing instructions that, when executed by the processor, cause the processor to perform the method of claim 8.

* * * * *